US005662686A

United States Patent [19]

Newsum

[11] Patent Number: 5,662,686

[45] Date of Patent: Sep. 2, 1997

[54] METHOD AND DEVICE FOR CORRECTING STRUCTURAL IMBALANCE IN A HUMAN SPINE

[76] Inventor: Lawrence E. Newsum, 25039 Narbonne Ave., Lomita, Calif. 90717

[21] Appl. No.: 585,641

[22] Filed: Jan. 16, 1996

[51] Int. Cl.[6] .......... A61F 5/00

[52] U.S. Cl. .......... 606/238; 606/237; 30/367

[58] Field of Search .......... 606/237, 238, 606/239, 182, 184, 185, 204, 201, 204.15; 30/366, 367, 368; 601/107, 108, 134

[56] References Cited

U.S. PATENT DOCUMENTS

| | | | |
|---|---|---|---|
| 2,048,220 | 7/1936 | Redding | 606/238 |
| 2,854,971 | 10/1958 | Williams | 606/238 |
| 4,116,235 | 9/1978 | Fuhr et al. | 606/238 |
| 4,268,927 | 5/1981 | Bridwell | 30/367 |
| 4,721,903 | 1/1988 | Harsch et al. | 30/367 |

FOREIGN PATENT DOCUMENTS

| | | | |
|---|---|---|---|
| 514924 | 3/1921 | France | 30/367 |
| 9115180 | 10/1991 | WIPO . | |

*Primary Examiner*—Michael Buiz

*Assistant Examiner*—Julian W. Woo

*Attorney, Agent, or Firm*—Charles H. Thomas

[57] ABSTRACT

A patient suffering from a condition of spinal muscle imbalance is treated by the application of controlled impact forces applied at specific points to the patient's neck. The point of application is to one side or the other of the spine at the rear of the patient's neck. The side to which the impact forces are applied is determined by areas of the body at which prior trauma has occurred that created the condition of spinal muscle imbalance. The forces are applied against the rear of the patient's neck directly below the head and at a force application point immediately at the splenius muscle and between the attachment of the superior border of the trapezius and the sternocleido mastoideus muscles to the patient's head. the impact forces are of a selected magnitude of between about four ounces and five pounds and are applied at a rising angle of about twenty five degrees toward the eye socket-temple area of the opposite side of the patient's head. The controlled impact forces are applied using a small, hand-held, mechanically operated implement in which a hammer is cocked and released to impart an impact force of precisely controlled magnitude. The implement can be easily adjusted to vary the selected magnitude of force to be applied as desired.

2 Claims, 7 Drawing Sheets

METHOD AND DEVICE FOR CORRECTING STRUCTURAL IMBALANCE IN A HUMAN SPINE

BACKGROUND OF THE INVENTION

1. Field of the Invention

The present invention relates to a method for balancing the muscles of the spine of a patient suffering from a condition of spinal muscle imbalance, and a therapeutic treatment instrument for performing the method of treatment.

2. Description of the Prior Art

Over the course of life people experience various events which subject parts of their bodies and muscles in their bodies to trauma of varying degrees. When the body is subjected to significant trauma, such as cutting or tearing of muscles, tendons, or ligaments; broken bones; severe contusions; and other physically traumatic injuries to the human body, the healing process within the body is sometimes accompanied by alterations to the muscles that hold the spine in substantially center alignment relative to the patient's body. That is, healing occurs such that some of the muscles acting upon the spine exert inadequate forces, while other muscles may exert forces that are overly strong. As a result, the spine of a patient, when viewed from the front or back, is no longer vertically aligned directly beneath the patient's head, but to the contrary, is pulled inordinately to the left or right at locations between the spine extremities where the spine joins the patient's skull and where the spine terminates in the tail bone.

Even slight deviations of proper spinal muscle balance can produce significant physical or emotional problems in some patients. Muscular imbalance of the spine often leads to excessively frequent or chronic backaches and can also produce conditions of chronic anxiety as well as pains in the patient's extremities.

An imbalance of the spinal muscles imparts laterally acting forces on the spine. These lateral forces deflect portions of the spine significantly from proper alignment in a vertical fore and aft plane bisecting the patient's body. A deformation of the spine is both painful and debilitating. The patient cannot freely move without significant pain in performing even mundane, every-day activities such as standing, sitting, walking, and turning.

SUMMARY OF THE INVENTION

According to the present invention it has been discovered that an imbalance of spinal muscles can be corrected by applying controlled amounts of force to specific locations on the patient's body. Application of controlled forces in this manner causes a relaxation of muscles that otherwise tend to remain in an unnaturally contracted or partially contracted condition due to prior traumatic events. When controlled impact forces are properly applied to the correct locations on the patient's body, relief of excessive muscular stress occurs almost immediately. A regular regimen of application and reapplication of controlled impact forces will result in a permanent or at least long-term relief of spinal muscle imbalance. As a consequence, even though the alignment of the spine may at one time have been severely distorted, therapeutic treatment by the application of controlled impact forces according to the system of the invention will almost completely reverse lateral spinal distortions. This course of treatment has very substantial physiological and psychological benefits for the patient.

The controlled impact forces are applied at a specific location and in a specific direction on the patient's body. The controlled impact forces should not exceed five pounds, but should be greater than a few ounces if they are to have any beneficial effect. The controlled impact force is applied to the rear of the patient's neck adjacent one side of the spine and directly beneath the patient's head. The side of the neck to which the force is applied is normally on the same side of the body at which the patient has experienced trauma that has lead to the spinal muscle imbalance. However, during a course of treatment the situation in some cases reverses itself, thus requiring the application of controlled impact forces on the opposite side of the neck. The selection of the proper side to which to apply the controlled impact force may be determined by performing certain body manipulations of the patient's limbs which will hereinafter be described. Once the determination has been made as to the side of the patient's neck to which the controlled impact force should be applied, it is important to then locate the precise impact force application point.

A controlled amount of impact force of no greater than five pounds magnitude is applied at a force application point located immediately below one side of the patient's head and between the attachment of the superior border of the trapezius and the sternocleido mastoideus to the patient's head. The impact force is thereby directed against the splenius muscle that lies between the sternocleido mastoideus and trapezius muscles. The force is applied in an inferior to superior direction toward the eye socket-temple area of the opposite side of the patient's head. This is at an upwardly and forwardly rising angle of about 25° above horizontal. The repeated application of a controlled amount of impact force in this manner will result in balancing of the muscles of the spine of a patient suffering from a condition of spinal muscle imbalance. The therapeutic treatment technique of the invention may be performed while the patient is in a supine, a prone, or a standing position. The repeated impact forces stimulate the patient's nerves to create a beneficial physiological response.

The therapeutic treatment of the invention may commence with the patient in the prone position. To start, the relative lengths of the patient's legs are checked while the patient lies prone. If an inequality of leg length is noticed, a controlled impact force is applied to the patient's neck on one side of the head just rearwardly of the mastoid sternocleido mastoideus muscle and immediately below the skull. Care should be taken to apply the force to the neck, and not against the skull which is located immediately adjacent thereto. To properly locate the point of application, areas of prior stress should be palpated by rubbing or the application of pressure thereto. The correct point of force application lies at the splenius muscle between the attachment of the superior border of the trapezius and the sternocleido mastoideus muscles to the head. This small area is called the medulla contact area.

Once the proper point of application has been located, it is important for the impact force to be properly directed. The line of drive of the controlled impact force is forwardly and upwardly across the fore and aft plane bisecting the patient's skull and toward the opposite eye socket or temple area.

Using the controlled impact force application instrument of the invention, one or two impact forces are applied to the neck of the patient. The length of the patient's legs are again checked. If the legs are not in balance, the same procedure should be repeated, but on the opposite side of the patient's neck.

If the attending physician or chiropractor applies the controlled impact force at the proper point in the medulla contact area and at the proper angle, the patient's legs will balance. That is, they will return to a condition of equal length. The patient's legs should not be bent until the attending physician or chiropractor has determined the proper side of contact for the application of controlled impact forces because old ankle, knee, or hip injuries can create a negative response. Once the proper site of contact and line of drive for the controlled impact forces has been determined, the ankles, knees, hips can be flexed. Also, the attending physician or chiropractor should press on all vertebrae to locate areas of weakness as well. Once all of the areas of weakness in the prone position have been determined, the patient is requested to turn over and assume the supine position.

While lying in the supine position in a straight alignment the patient is requested to bring his or her hands above the head, palms turned inward. The attending physician or chiropractor stands directly in line with the patient's body facing the patient's head and aids the final movement of the patient's arms by bringing the arms equal distances from the side of the patient's head. This step is critical, and regardless of how the elbows bend, the arms should be brought the same distance from the sides of the head. It is imperative that the patient's shoulders and arms are totally relaxed while this is done. The attending physician or chiropractor should not even look at the patient's hands until the arms of the patient are in transverse linear alignment with each other at equal distances from the side of the patient's head.

The attending physician or chiropractor should then determine and note any difference in arm length. The patient is then requested to turn his or her head to one side. This provides access to the proper contact area at the back of the patient's neck. Using a special implement, hereinafter described, a controlled impact force is then applied to the exposed side of the patient's neck immediately beneath the patient's head. The lengths of the patient's arms should again be rechecked. If the arms at this time balance, a muscle test should be performed to verify. If the arms remain unbalanced, the controlled impact force should then be applied to the opposite side of the patient's neck. Again, the length of the patient's arms are rechecked and the muscle test is again preformed once the controlled impact force has been applied.

The lengths of the patient's legs should then be checked for equality. If one leg is longer than the other, the controlled impact force should again be applied to one side of the patient's neck. If no corrective change is noted, the force should be applied to the opposite side of the patient's neck. Once positive results are achieved indicating a return of the patient's arm lengths and leg lengths to equal, balanced positions, the areas of prior trauma should be restressed. This is done by having the patient raise his or her head upwards as far as possible and to thrust the head repeatedly until the spine stabilizes. The patient should then perform a head rotation from side to side in the same manner.

While lying in the supine position, the patient should then stress the areas of prior trauma. These areas may be identified by scars, organ depots, including eyes, ears, nose, throat, the jaw, gums, and the scalp on the head. If these areas are clear, the finger joints should then be stressed, as should the wrists, and elbows by flexion and extension under force. Any area of prior injury can be stressed by vigorously rubbing it for a few seconds or by applying pressure to it. When all of the areas of weaknesses have been detected and controlled amounts of impact force applied to the rear of the patient's neck in the manner previously described, the patient should then stand.

To achieve spinal reconstruction, the spinal joints must be moved by following a prescribed procedure. There can be no injury according to this procedure, since all movement of the spine is achieved through the patient's muscles. When the patient's muscles move the bones of the spine, correction is more permanent. Indeed, it is the muscles that must hold the spine in place.

With the patient standing upright, the head of the pectoral muscle is first tested. The deltoid muscle should not be used as a test location, since it is too strong.

The patient extends his or her arms with elbows and wrists straight, not bent. The patient's hands are turned so that the thumbs are turned towards the floor. The patient stands on his or her toes briefly. The patient should then twist one ankle under the leg, and then the other. Controlled amounts of impact force are applied to the medulla contact area following each stress placed on the patient.

The patient should then twist as far as possible from the right to the left or from left to right. The patient should flex and extend the torso as far as possible. Again, following each stress, controlled impact forces of no greater than about five pounds are applied. Thereafter, the patient's torso undergoes lateral flexion. Again, controlled impact forces are applied to the medulla contact area.

By performing localized muscular stress and taking corrective action by the application of controlled amounts of impact force, low back problems in a patient can be corrected. When all lower extremities are cleared and balanced, the patient turns his or her head to the contact point side as far as possible while lifting the chin and high as possible. The patient should be rechecked and corrective impact forces applied as needed. This procedure is repeated until the spinal muscles have stabilized.

Spinal muscular imbalance can arise from a variety of sources. Such muscular imbalance can occur due to the result of hiatal hernias. To achieve muscle balance correction due to a hiatal hernia condition, the patient should stress the hiatal area while lying in the supine position. Controlled impact forces are then applied to the medulla contact area.

Spinal muscle imbalance can also occur as a result of migraine Headaches. To correct for this condition, gastric, cranial, and occipital areas should be checked carefully.

Bursa pain is also a source of spinal muscle imbalance. Such pain is commonly the result of problems in other areas of the body. Areas of old injury, such as sprains, surgeries, cuts, and skull injuries, should always be cleared. Pain is often due to interference that acts quite remote from the area of the symptoms.

Sciatica pain is another source of spinal muscle imbalance. To alleviate such conditions, all organs should be checked for weakness, including the kidneys, heart, and pancreas.

Spinal muscle imbalance may also result from emotional as well as physical stress. To remedy spinal muscle imbalance caused by emotional stress, the procedure is very similar to the correction for stress of physical areas on the body. Specifically, to correct for spinal muscular imbalance due to emotional stress, an emotional release must be elicited.

In correcting for an emotional problem, it is important for the patient to feel, that is recreate, the emotional problem, not just think about it. Memory creates feeling and feelings recreate the problem. Correction for stress due to emotional problems is often quite difficult, since the patient will frequently have difficulty bringing the feeling, that is the emotion, back.

Emotional release is achieved by first having the patient recreate the problem emotionally. The subject should be instructed to think of an emotional problem that they have experienced. This can be something that was either done to the patient or something that the patient has done to someone else. The patient should be checked for weaknesses by pressing on a suspect area of the body. When those weaknesses are located a controlled amount of impact force of no greater than about five pounds is repeatedly applied to the medulla contact area until there is no further weakness.

In one broad aspect the present invention may be considered to be a method of balancing the muscles of the spine of a patient. According to the method of the invention a controlled amount of impact force of no greater than about five pounds is applied to the rear of the patient's neck beneath one side of the patient's head and against the splenius muscle adjacent the attachment of the sternocleidal mastoideus muscle to the base of the skull. This controlled impact force is directed forwardly and upwardly in linear alignment with the eye socket-temple area on the opposite side of the patient's head. The exact proper alignment will vary slightly from patient to patient.

In another broad aspect the invention may be considered to be a method of therapeutically treating a patient for spinal muscle imbalance. According to the method of the invention stress is applied to an area of prior trauma to a patient's body. Then, to the rear of the patient's neck adjacent one side of the patient's head a controlled amount of impact force of no greater than five pounds magnitude is applied at a force application point called the medulla contact area. The medulla contact areas are located immediately below the sides of the patient's head and between the attachment of the superior border of the trapezius and the sternocleidal mastoideus muscles to the patient's head. The controlled impact force is applied in an inferior-to-superior direction toward the eye socket-temple area of the opposite side of the patient's head.

In still another broad aspect the invention may be considered to be a therapeutic treatment device for applying a predetermined magnitude of impact force to muscles beneath the base of the rear of the head of a patient on a selected side of a patient's spine. The therapeutic treatment device is composed of an elongated, hollow body, a hammer, a tensioning spring, a push rod, a clutch mechanism, and a clutch spring.

The hollow body is an elongated structure having an open end and an opposite, axially closed end and defining between the open and closed end an annular guide ring having a central guide aperture therewithin. The hammer is wider than the central guide aperture and is disposed for reciprocal movement within the hollow body. The hammer is located between the guide ring and the closed end.

The compressed tension spring is located in the hollow body between the hammer and the closed end. The push rod is longitudinally reciprocal relative to the hollow body and emanates from the hollow body through the open end thereof. The push rod has a proximal end entrapped within the hollow body and a distal end projecting therefrom for contacting the muscles beneath the head of the patient. The clutch mechanism is also located within the hollow body and engages the hammer within the hollow body. The clutch mechanism releases the hammer at a predetermined distance from the guide ring. The compressible clutch spring is disposed within the hollow body between the guide ring and the push rod. The clutch spring acts to bias the clutch mechanism and the push rod toward the open end of the body.

The invention maybe described with greater clarity and particularity by reference to the accompanying drawings.

DESCRIPTION OF THE EMBODIMENTS AND IMPLEMENTATION OF THE METHOD

FIGS. 1, 2, 2A, and 3 illustrate the locations for application of a controlled amount of impact force, and a special purpose, therapeutic treatment instrument 10 for applying that force. The therapeutic treatment instrument 10 is illustrated in detail in FIGS. 4–10.

Figure 5:
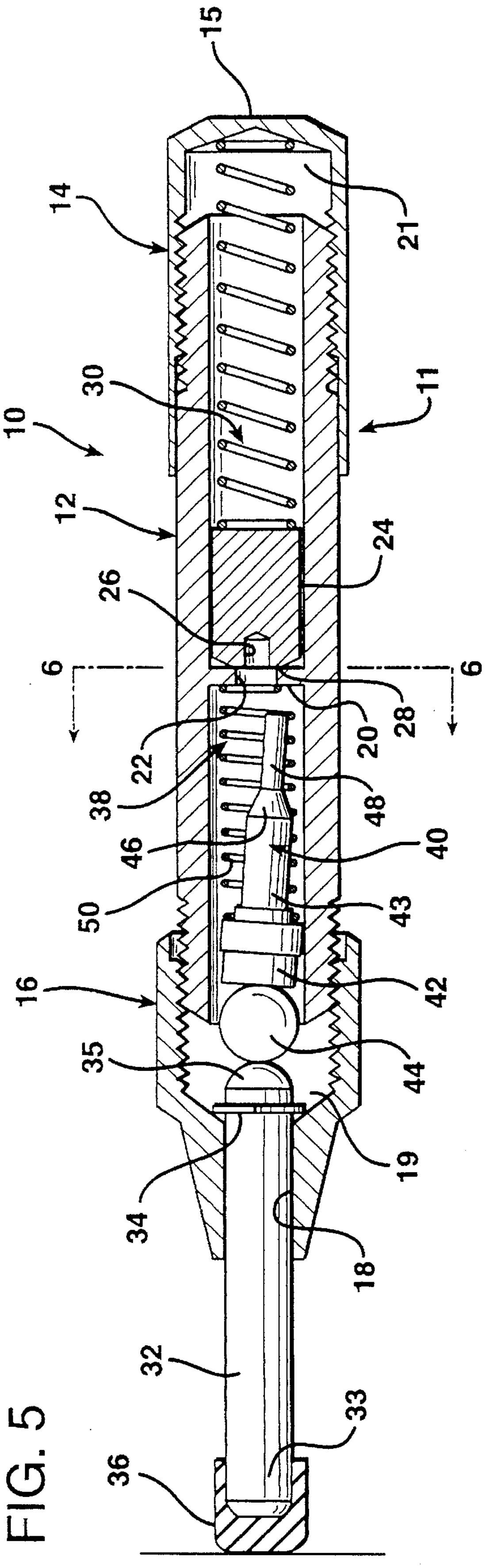
FIG. 5 is a sectional elevational detail of one preferred embodiment of a therapeutic treatment device according to the invention employing the internal components of FIG. 4.
Figure 10:
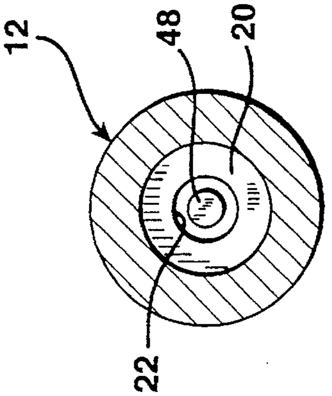
FIG. 10 is a transverse sectional view taken along the lines 10—10 of FIG. 9.

FIG. 5 illustrates the therapeutic treatment instrument 10 in a relaxed condition. The instrument 10 is constructed with an elongated, hollow body 11 formed by a tubular, barrel-shaped section 12 that is externally threaded at both ends, a cup-shaped, internally threaded adjustment cap 14 engaged on one end of the tubular barrel 12, and an annular, internally threaded thimble or nipple 16. The thimble 16 forms an opening 18 thus defining the open end 19 of the hollow body 11. The transverse end wall 15 of the adjustment cap 14 defines the opposite, axially aligned, closed end 21 of the hollow body 11. Between the open end 19 and the closed end 21 of the hollow body 11 the tubular barrel 12 defines an annular guide ring 20 that forms a central, axially aligned, circular guide aperture 22 therewithin.

Within the closed end of the hollow body 11 there is a generally cylindrical, slug-shaped piece of metal serving as a hammer 24. The hammer 24 has a central, axial bore that forms a pocket 26 defined in its flat, annular surface 28 that faces the annular guide ring 20. The hammer 24 is disposed for reciprocal movement within the hollow body 11 and is located between the guide ring 20 and the closed end 21 of the hollow body 11. A tensioning spring 30 is located in the hollow body 11 between the hammer 24 and the transverse end wall 15 of the adjustment cap 14. When the instrument 10 is in the relaxed condition depicted in FIG. 5, the tensioning compression spring 30 is under a minimum compression force, as the hammer 24 is forced completely away from the transverse end wall 15 of the adjustment cap 14 and into abutment against the guide ring 20.

A cylindrical push rod 32 is located at the opposite end of the hollow body 11, remote from the adjustment cap 14. The push rod 32 is longitudinally reciprocal relative to the hollow body 11. The push rod 32 has a distal end 33 that emanates from the hollow body 11 through the opening 18 in the thimble 16. The push rod 32 also has an opposite proximal end 35 that is rounded in a semispherical configuration and captured within the thimble 16. The proximal end 35 is retained within the hollow body 11 by means of a C-ring 34 that engages a radial groove in the outer surface of the proximal end 35 of the push rod 32. The distal end 33 of the push rod 32 projects from the thimble 16 of the hollow body 11 and is provided with a concave, cup-shaped, hard vinyl tip 36. The tip 36 on the distal end 33 of the plunger or push rod 32 increases the area of application of the impact force when the instrument 10 is utilized in the manner depicted in FIGS. 2, 2A, and 3.

Figure 4:
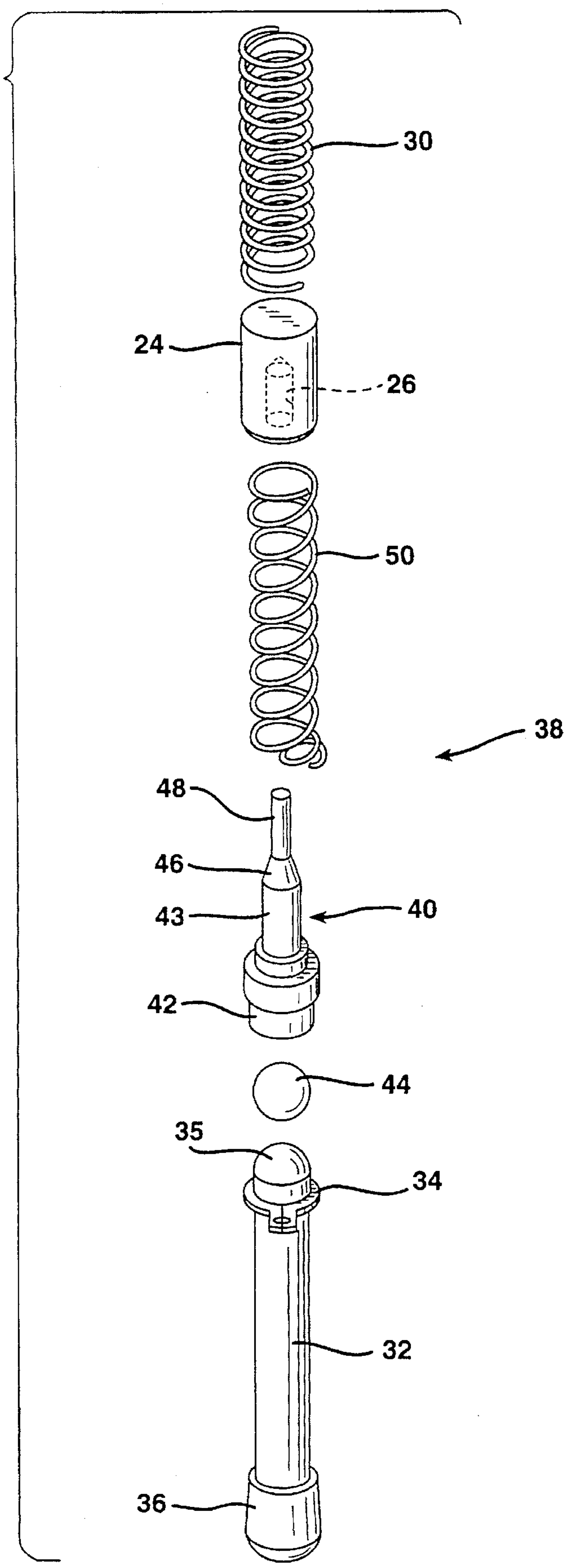
FIG. 4 is an exploded view of the internal components of a therapeutic treatment device for applying controlled impact forces to the rear of the neck of a patient to correct for muscle imbalance.

The instrument 10 is also comprised of a clutch mechanism indicated generally at 38 in FIGS. 4 and 5. The clutch mechanism 38 is comprised of an elongated member 40 that has a generally disc-shaped base 42. The base 42 of the elongated member 40 pivotally seats upon the proximal end of the push rod 32 through an intervening spherical, metal ball bearing 44. The elongated member 40 also includes a cylindrical body portion 43 adjacent the base 42. The cylindrical body portion 43 terminates at an intermediate, frustoconical-shaped cam region 46 that forms a transition between the body portion 43 of the elongated member 40 and a slender pin 48 which projects from the cam region 46. The diameter of the pin 48 is significantly less than the diameter of the body portion 43 of the elongated member 40.

The clutch mechanism 38 also includes a clutch spring 50. The clutch spring 50 is a wire spring helically wound off center as best depicted in FIG. 4. The clutch spring 50 is disposed about the elongated body 40 of the clutch mechanism 38. The clutch spring 50 is longitudinally compressed and acts against the base 42 of the elongated member 40 and the guide ring 20 of the hollow, annular body 11. The clutch spring 50 bears against the guide ring 20 and against the base 42 of the elongated clutch body 40 so as to normally urge the elongated body 40 away from the hammer 24. This pushes the push rod or plunger 32 out of the opening 18 in the thimble 16 so as to fully extend the distal end 33 of the plunger or push rod 32 from the hollow body 11 as depicted in FIG. 5. Due to its off-center winding, the clutch spring 50 exerts a laterally deflecting force on the elongated body 40, as most completely depicted in FIGS. 5 and 6.

Figure 1:
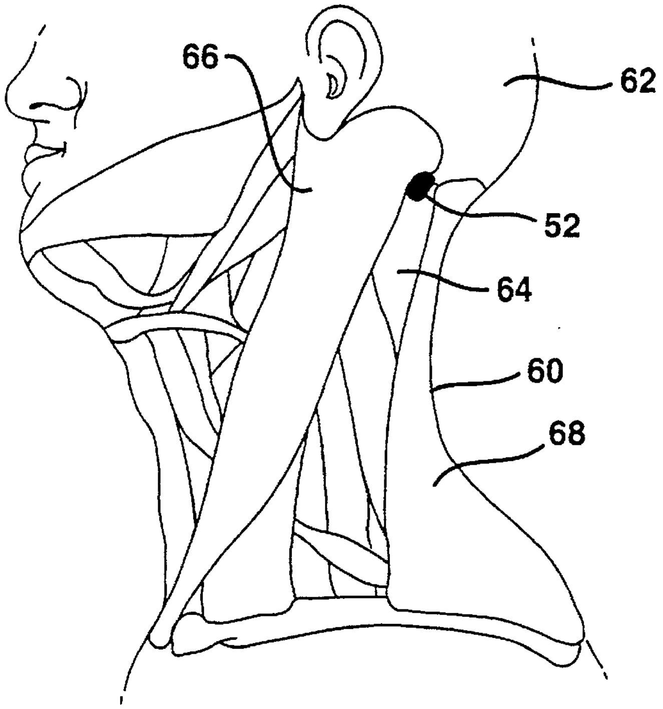
FIG. 1 is a perspective lateral view of the muscles of one side of the neck showing the medulla contact area.

To operate the therapeutic treatment instrument 10, the tip 36 of the distal end 33 of the push rod 32 is placed against the medulla contact area 52 at the rear of the neck 60 of the patient. The medulla contact area 52 is best shown in FIG. 1. FIG. 1 diagrammatically illustrates the muscles and other body components in the immediate vicinity of the medulla contact area 52. Specifically, there is an medulla contact area 52 located on each side of the rear of the patient's neck 60 near the upper extremity thereof where the neck 60 joins the head 62 at the base of the patient's skull. The medulla contact area 52 is located at the top of the splenius muscles 64 adjacent the attachment of the sternocleido mastoideus muscles 66 at the base of the patient's skull 62. The medulla contact area 52 is located at the upper extremity of the appearance of the splenius muscle 64 at the gap between the sternocleido mastoideus muscle 66 and the superior border of the trapezius muscle 68.

Figure 2:
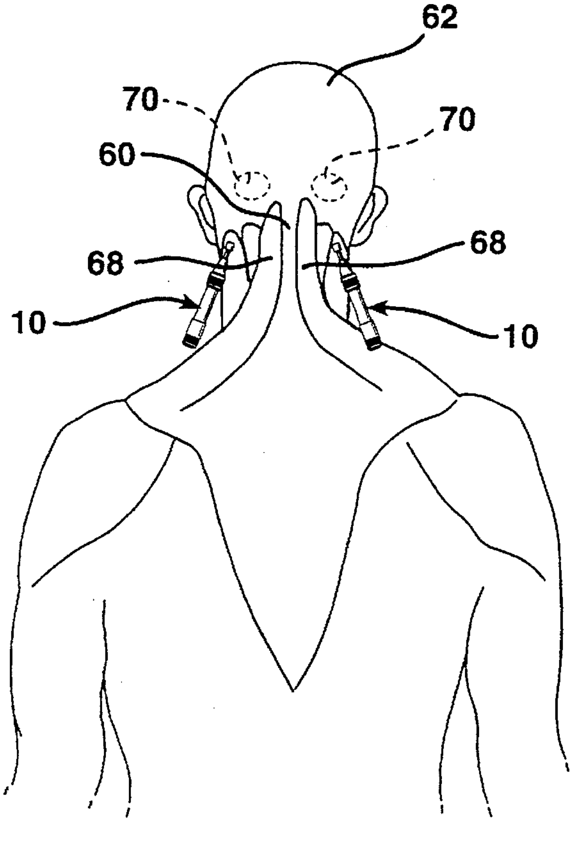
FIG. 2 is a rear elevational view illustrating the manner of application of controlled impact forces according to the invention.
Figure 2A:
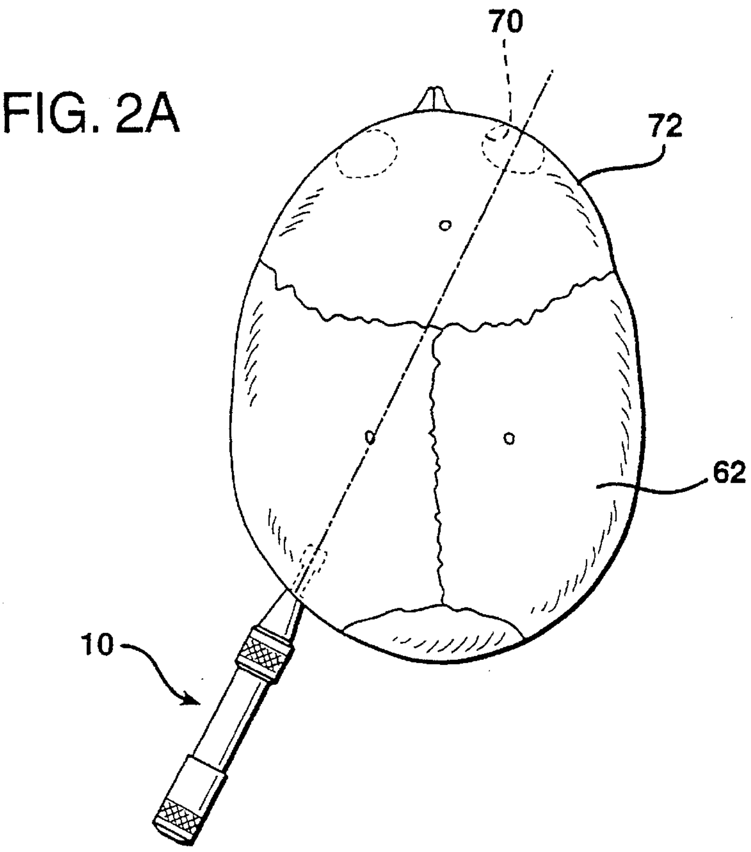
FIG. 2A is a top plan view illustrating the application of controlled impact forces according to the invention.
Figure 3:
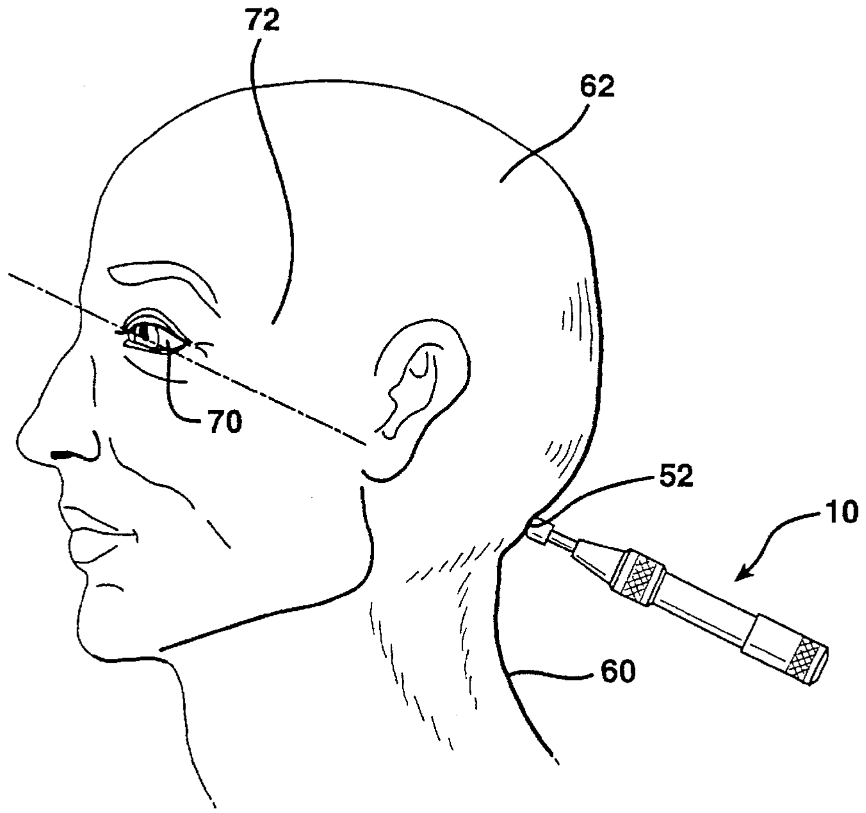
FIG. 3 is a side elevational view illustrating the application of controlled impact forces according to the invention.
Figure 8:
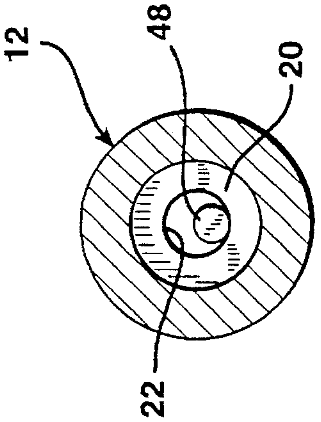
FIG. 8 is a transverse sectional view along the lines 8—8 of FIG. 7.
Figure 6:
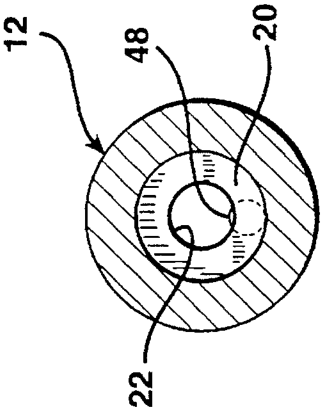
FIG. 6 is a transverse sectional view taken along the lines 6—6 of FIG. 5.
Figure 7:
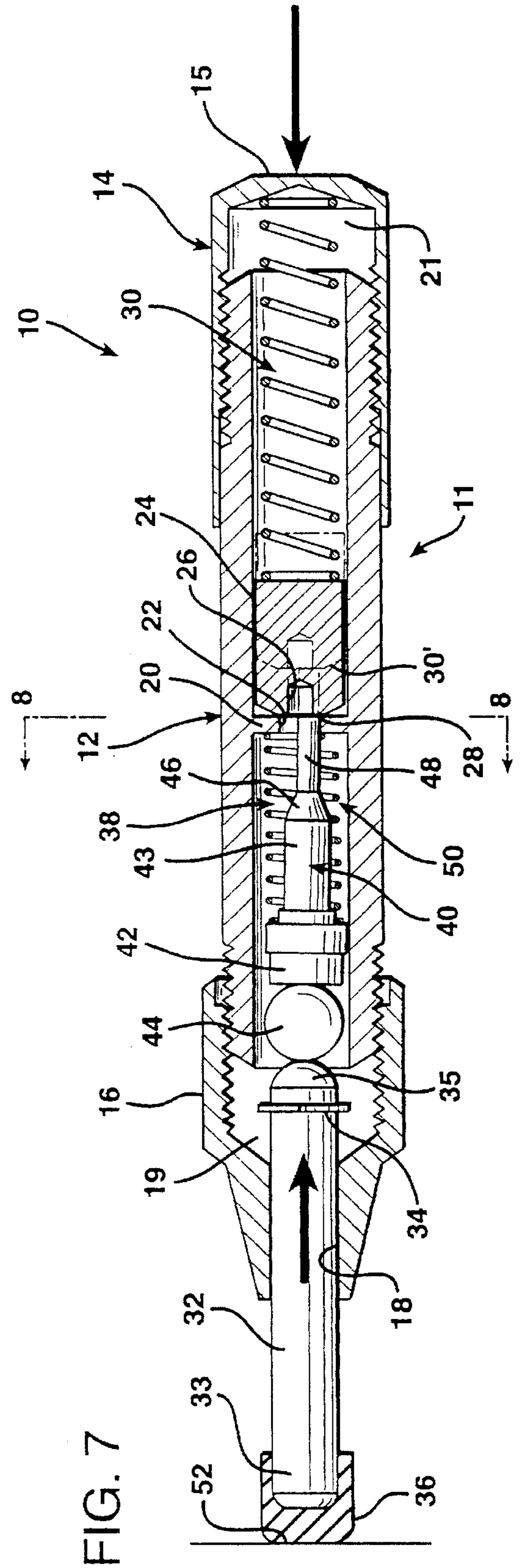
FIG. 7 is a sectional elevational detail showing the initial compression of the therapeutic treatment device of FIG. 5.

FIGS. 1 through 3 illustrate the controlled impact therapeutic instrument 10 used according to the method of the invention. By grasping the exterior of the hollow body 11 the administering physician or chiropractor presses the structure of the hollow body 11 toward the medulla contact area 52 as illustrated in FIGS. 2, 2A, and 3. As force is applied on the outer surface of the hollow body 11 toward the medulla contact area 52, the clutch spring 50 is partially compressed so that the pin 48 of the elongated clutch body 40 enters the central opening 22 in the guide ring 20, but in off-center alignment relative thereto due to the off-center winding of the clutch spring 50, as illustrated in FIG. 8. Once the pin 48 passes through the opening in the guide ring 20, a portion of the end of the pin 48 bears in abutment against the transverse, flat surface 28 of the hammer 24 surrounding the pocket 26.

With continued longitudinal force pressing the hollow body 11 toward the distal end 33 of the push rod 32 which in turn presses against the medulla contact area 52 through the tip 36, the clutch spring 50 is compressed more and more. With continued advancement the pin 48 of the elongated clutch body bears against the flat, transverse surface 28 of the hammer 24 and begins to force the hammer 24 away from the guide ring 20. This movement compresses the tensioning spring 30, as illustrated in phantom at 30' in FIG. 7.

With continued pressure on the hollow body 11 toward the distal end 33 of the push rod 32, the hammer 24 is forced increasingly toward the transverse end wall 15 of the adjustment cap 14. This further compresses the tensioning spring 30. Because the clutch spring 50 is helically wound off center, the pin 48 continues to bear against the flat surface 28 surrounding the pocket 26 in the end face of the hammer 24 until the cam surface 46 of the elongated body 40 reaches the guide ring 20. At this point further longitudinal compressive force on the hollow body 11 toward the medulla contact area 52 causes the cam surface 46 of the elongated member 40 to ride up on the edge of the guide ring 20, overcoming the laterally deflecting force of the clutch spring 50. As the cam surface 46 rides up over the edge of the guide ring 20, the elongated member 40 rotates into axial alignment with the pocket 26 in the hammer 24. Smooth rotation is aided by virtue of the pivotal movement permitted by the spherical ball bearing 44 between the base 42 of the clutch body 40 and the push rod 32.

Figure 9:
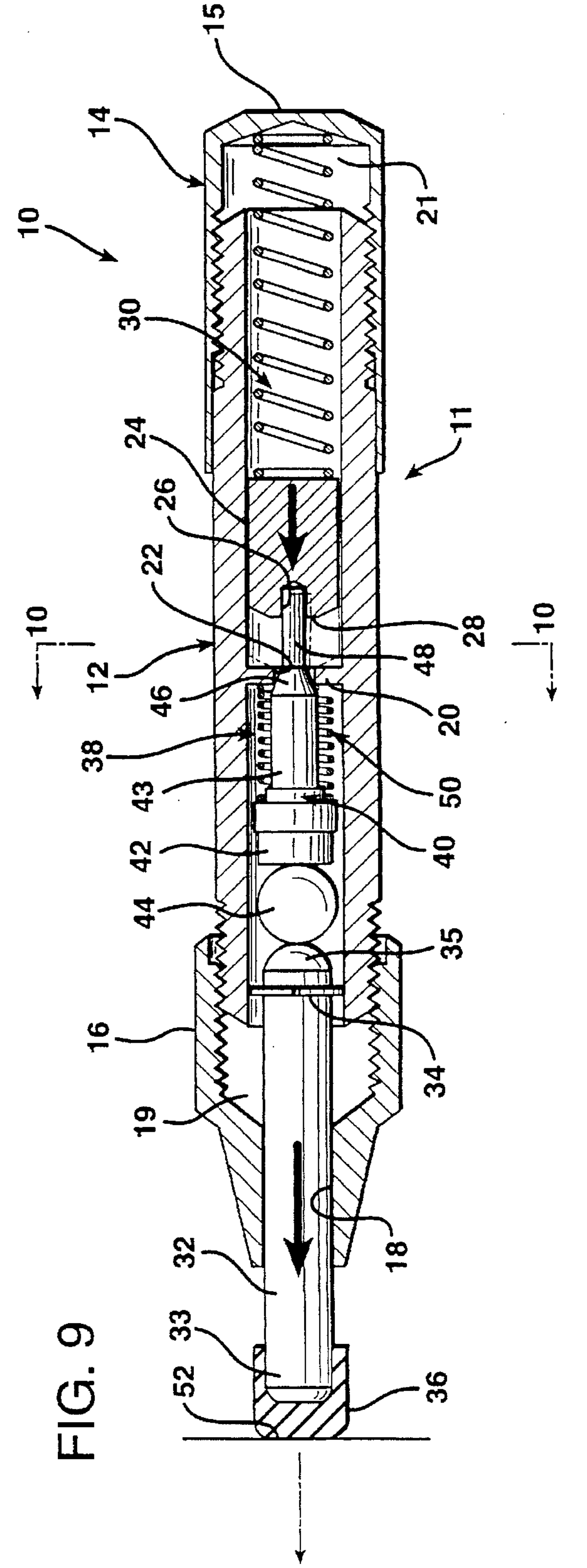
FIG. 9 illustrates the operation of the therapeutic treatment device of FIG. 5 to produce a controlled impact force of predetermined magnitude.

As the cam surface 46 passes the edge of the guide ring 20 as illustrated in FIG. 9, lateral deflection of the pin 48 diminishes until the pin 48 reaches a position in which it resides in central axial alignment relative to the pocket 26 in the hammer 24. When this occurs the hammer 24 is released, since the end of the pin 48 no longer bears against the surface 28 surrounding the pocket 26 in the face of the hammer 24, but rather is then axially aligned with the pocket 26. When this occurs, the compressed tensioning spring 30, which has been increasingly compressed by the longitudinal force on the hollow body 11, suddenly forces the hammer 24 to the left, as viewed in FIG. 9, a distance equal to the depth of the pocket 26. The hammer 24 thereupon exerts a controlled impact force upon the pin 48, which in turn transmits that force to the remaining portion of the elongated member 40 and to the push rod 32 through the spherical ball bearing 44.

As is evident from the drawings, the magnitude of the controlled impact force can be variedby adjusting the degree of advancement of the adjustment cap 14 relative to the barrel 12. This varies the extent to which the tensioning spring 30 is compressed as the hammer 24 is cocked by the clutch mechanism 38. The farther the adjustment cap 14 is threadably advanced to the left on to the barrel 12, as viewed in FIG. 5, the greater will be the extent of compression of the tensioning spring 30 and hence the force applied to the hammer 24 when the clutch mechanism 38 releases the hammer 24. Conversely, the impact force can be reduced by backing the adjustment cap 14 off of the barrel 12 to the right, as viewed in FIG. 5, to thereby reduce the extent to which the tensioning spring 30 is compressed by the clutch mechanism 38.

The adjustment cap 14 thereby serves as a means for applying an adjustable preload on the tensioning spring 30. The adjustment cap 14 defines and controls the predetermined magnitude of impact force applied to the patient's neck. The impact force applied through the hammer 24 should not exceed five pounds, and should be at least four ounces in order to have any beneficial effect when applied to the medulla contact area 52.

Prior to applying controlled impact forces using the implement 10 the area of prior trauma which resulted in spinal muscle imbalance is first stressed. This is easily accomplished by rubbing the area of prior trauma. The therapeutic treat instrument 10 is then manipulated in the manner previously described to repetitively apply controlled impact blows of between about four ounces and five pounds of force each to the medulla contact area 52.

As illustrated in FIG. 2, 2A, and 3, the hard tip 36 at the distal end 33 of the push rod 32 is positioned in contact with the medulla contact area 52. The body 11 of the therapeutic treatment instrument 10 is aligned so that the push rod 32 is directed forwardly and upwardly in linear alignment toward the area 70 of the eye socket and the temple area 72 on the side of the patient's head 62 opposite the side of the neck 60 against which the controlled impact force is applied. The therapeutic instrument 10 is aligned at an angle inferior to superior of about 25° directed toward the opposite eye socket 70 or temple 72. The hollow body 11 of the instrument 10 is thereupon abruptly pressed toward the medulla contact point 52. As previously explained, the longitudinal force of the clutch spring 50 is overcome, and the pin 48 bears against the flat surface 28 to push the hammer 24 back toward the closed end 21 of the hollow body 11 formed by the transverse end wall 15 of the adjustment cap 14. This movement compresses the tensioning spring 30.

Movement of the hollow body 11 toward the patient's neck 60 is continued in this manner until the cam surface 46 of the elongated member 40 rides up and over the edge of the guide ring 20 forming the opening 22. At this point the base 42 of the elongated clutch body 40 rotates smoothly on the spherical ball bearing 44, bringing the pin 48 into axial alignment with the pocket 26 in the hammer 24. As the tip of the pin 48 slips off of the transverse surface 28 and into the pocket 26, the force of the compressed tensioning spring 30 is released and the hammer 24 is thrust away from the transverse end wall 15 of the cap 14 and into contact with the transverse end of the pin 48. A longitudinal blow is transmitted through the elongated member 40 and the spherical ball bearing 44 to the push rod 32, thereby delivering a precisely controlled impact force to the medulla contact area 52. The instrument 10 is manipulated in this same fashion repetitively three or four times to deliver a series of controlled blows to the medulla contact area 52.

Figure 12:
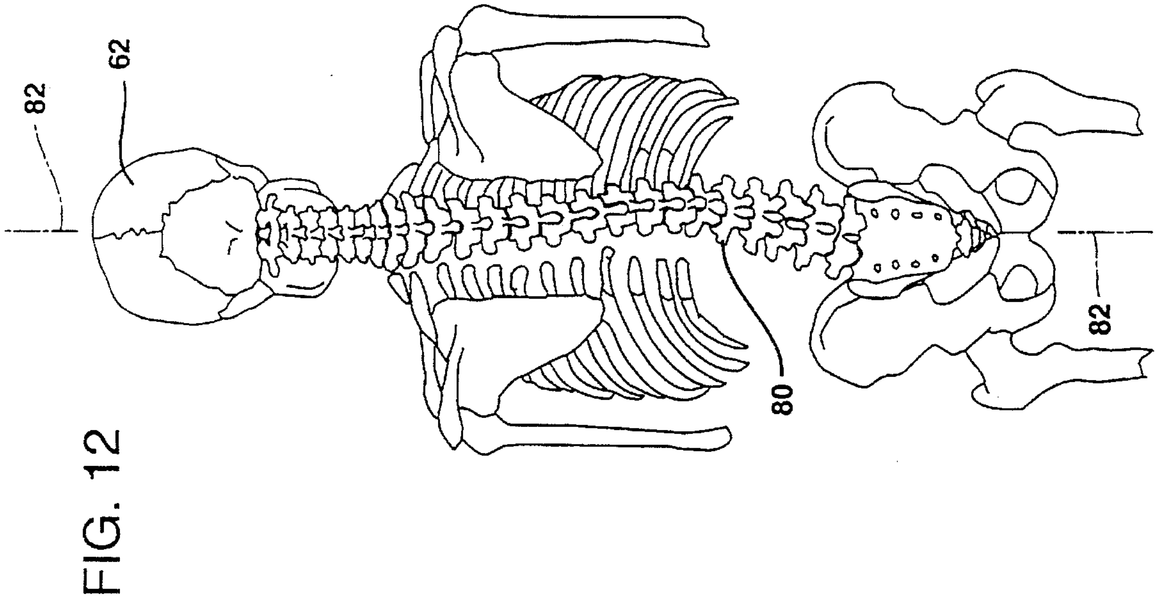
FIG. 12 is a elevational diagram of the spine of a patient in which significant muscle imbalance exists.

With repeated treatment according to the invention, dramatic changes in spinal muscle imbalance have been noted. For example, FIG. 12 is a drawing of an x-ray showing the skeletal structure of a patient suffering from spinal muscle imbalance prior to any treatment according to the invention. As illustrated in FIG. 12, the spine 80 is severely distorted and deflected from a proper position of alignment in a vertical, fore and aft plane 82 that passes through and bisects the patient's body. The spine 80 is held in the condition depicted in FIG. 12 by an imbalance of the muscles acting upon the spine 80. The imbalance may result from prior physical or emotional trauma.

Figure 13:
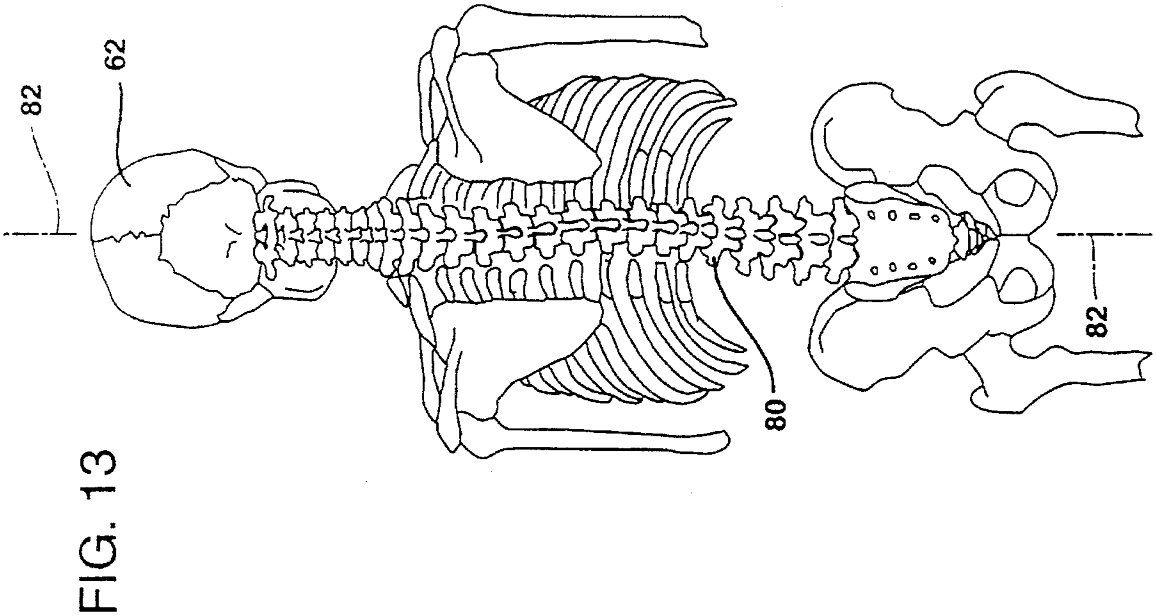
FIG. 13 is a sectional elevational diagram of the spine of the same patient following corrective therapeutic treatment according to the invention.

FIG. 13 is a drawing of an x-ray illustrating the spine of the same patient after several weeks of treatment according to the invention. As illustrated in FIG. 13, the patient's spine 80 is no longer severely deformed, but to the contrary has returned to nearly balanced, normal alignment in the vertical fore and aft plane 82. The patient who was the subject of the x-rays of FIG. 12 and 13 experienced a substantial reduction in spinal muscle pain and greatly enhanced spinal mobility from the inception of treatment according to the invention for the spinal condition depicted in FIG. 12 to the conclusion of treatment. At the conclusion of the treatment the patient's spinal orientation was almost totally corrected, as shown in FIG. 13.

Figure 11:
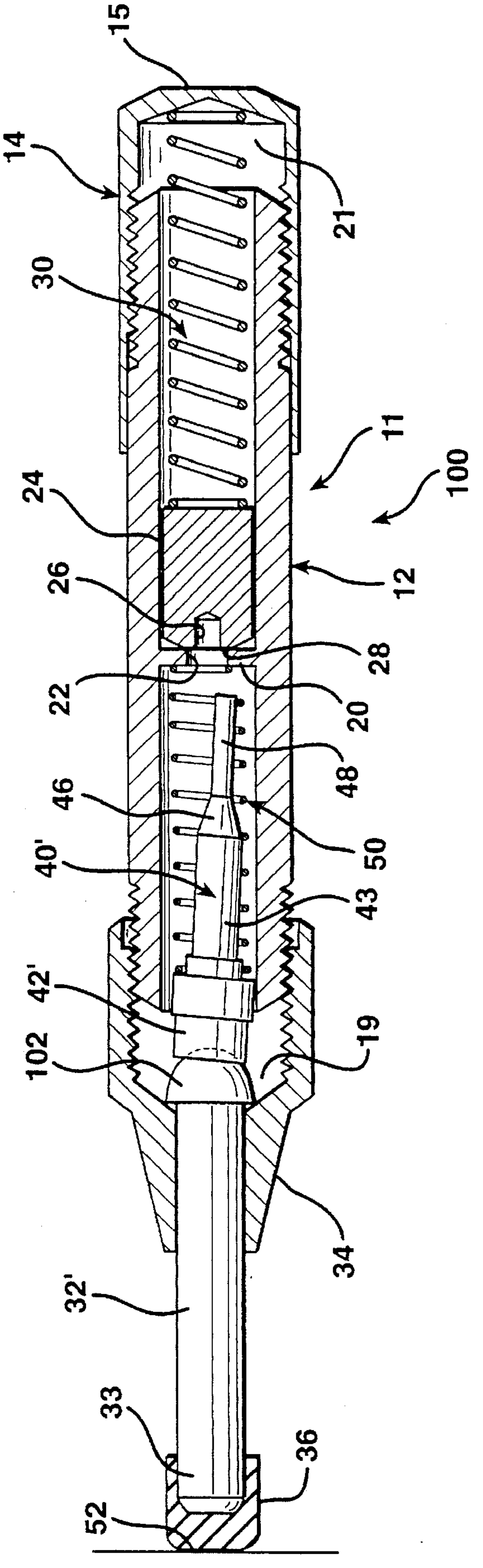
FIG. 11 is a sectional elevational view of a alternative embodiment of a therapeutic device according to the invention.

Therapeutic instruments of various design may be utilized to administer the controlled impact forces required according to the invention. While the embodiment of FIGS. 4–10 is a preferred embodiment, FIG. 11 illustrates an alternative embodiment of a different therapeutic instrument 100 constructed according to the invention. The instrument 100 is nearly identical to the instrument 10. However, the spherical ball bearing 44 has been omitted. Instead, the proximal end of the push rod 32 is formed with a slightly enlarged semispherical surface 102 having a diameter greater than that of the opening 18. This thus obviates the need for the C-clamp 34. Also, the exposed face of the base 42' of the elongated clutch member 40' is hollowed out to form a concave, surface of a radius of curvature that corresponds to the radius of curvature of the proximal end 102 of the push rod 32'. The base 42' of the elongated clutch member 40' is thereby able to pivot freely on the convex, semispherical surface of the proximal end 102 of the push rod 32' when the cam surface 46 interacts with the guide ring 20 in the manner previously described.

Undoubtedly, numerous variations and modifications of the invention will become readily apparent to those familiar with spinal muscle imbalance. Accordingly, the scope of the invention should not be construed as limited to the specific embodiments nor to the manner of implementation of the method depicted and described.

I claim:

1. A method of balancing the muscles of the spine of a patient comprising:

applying a controlled mount of impact force of no greater than about five pounds to the rear of a patient's neck beneath one side of the patient's head and against the splenius muscle adjacent the attachment of the sterno-cleido mastoideus muscle to the base of the skull and directing said force forwardly and upwardly in linear alignment with the eye socket-temple area on the opposite side of the patient's head, wherein said impact force is applied using a device formed of an elongated hollow body having an open end and an opposite, axially aligned, closed end, and an annular guide ring located between said open end and closed ends; a hammer disposed for reciprocal movement within said hollow body and located between said guide ring and said closed end; a compressed tensioning spring located in said hollow body between said hammer and said closed end of said body; a push rod longitudinally reciprocal relative to said hollow body and emanating from said open end of said hollow body and having a proximal end entrapped within said hollow body and a distal end projecting therefrom for contacting the rear of a patient's neck; a clutch mechanism for cocking said hammer within said hollow body and which releases said hammer at a predetermined distance from said guide ring when said push rod is forced toward said closed end of said hollow body to compress said tensioning spring; and a compressible clutch spring disposed within said hollow body and biasing said push rod toward said open end of said body; comprising the steps of:

placing said distal end of said push rod in contact with the rear of a patient's neck as aforesaid and pressing said hollow body toward said patient's neck to compress said tensioning spring until said clutch mechanism releases said hammer.

2. A method of therapeutically treating a patient for spinal muscle imbalance comprising:

applying stress to an area of prior trauma in a patient's body, and applying to the rear of said patient's neck adjacent one side of said patient's head a controlled mount of impact force of no greater than five pounds magnitude at a force application point immediately below said one side of said patient's head and between the attachment of the superior border of the trapezius and the sterno-cleido mastoideus muscles to said patient's head in an inferior-to-superior direction toward the eye socket-temple area of the opposite side of said patient's head, wherein said controlled force is applied with an implement formed with an elongated hollow body housing a hammer, a compressed tensioning spring for drilling said hammer, a clutch mechanism for releasing said hammer, and a plunger for operating said clutch mechanism and for receiving a blow from said hammer, by pressing said plunger against said force application point and pushing said hollow body toward said patient's neck until said clutch mechanism releases said hammer to apply said controlled impact force through said plunger.

* * * * *